United States Patent [19]
Inselburg et al.

[11] Patent Number: 6,024,966
[45] Date of Patent: Feb. 15, 2000

[54] **GENE ENCODING PROTEIN ANTIGENS OF *PLASMODIUM FALCIPARUM* AND USES THEREFOR**

[75] Inventors: Joseph W. Inselburg, Norwich, Vt.; David J. Bzik, Hanover, N.H.

[73] Assignee: Trustees of Dartmouth College, Hanover, N.H.

[21] Appl. No.: 08/335,204

[22] Filed: Nov. 7, 1994

Related U.S. Application Data

[60] Continuation of application No. 07/997,092, Dec. 29, 1992, abandoned, which is a division of application No. 07/870,806, Apr. 17, 1992, abandoned, which is a continuation of application No. 07/231,771, Aug. 12, 1988, abandoned.

[51] Int. Cl.$^7$ .................................................. A61K 39/015
[52] U.S. Cl. ................................... 424/268.1; 424/185.1; 424/272.1; 530/350; 530/395; 435/69.3
[58] Field of Search ...................... 530/350, 395; 424/88, 185.1, 268.1, 272.1; 435/69.3

[56] References Cited

U.S. PATENT DOCUMENTS 4,546,082  10/1985  Kurjan et al. ......................... 435/172.3

FOREIGN PATENT DOCUMENTS 8703882  7/1987  WIPO ............................ C07H 21/04

OTHER PUBLICATIONS

Inselburg et al Infect. Immun. vol. 59 pp. 1247–1250 (1991).
Mitchell Parasitology vol. 98 pp. 529–547 (1989).
Eisen in Immunology 2$^{nd}$ Edition, Harper & Row Publishers, Hagerstown PA (1980) p. 294.
Stedman's Medical Dictionary 25$^{th}$ Edition, Williams & Wilkens, Baltimore MD 21202 (1990) p. 1680.
Phillips et al Parasitology Today vol. 2 pp. 271–282 (1986).
Cox TIBTECH vol. 9 pp. 389–394 (1991).
Horii et al Mol. Biochem Parasitol. vol. 30 pp. 9–18 (1988).
Banyal et al Am. J. Trop. Med. Hyg. vol. 34 pp. 1055–1064 (1985).
Weber et al Molecular Strategies of Parasitic Invasion.
Delplace Mol. Biochem. Parasitol. vol. 23 pp. 193–201 (1987).
Maniah's et al Molecular Cloning: A Laboratory Manual Cold Spring Harbor Laboratory CSH, NY (1982) pp. 310–352 & 404–433.

*Primary Examiner*—Thomas M. Cunningham
*Attorney, Agent, or Firm*—Giulio A. DeConti, Jr., Esq.

[57] ABSTRACT

A *Plasmodium falciparum* gene encoding immunogenic SERA protein has been isolated by a) systematically screening a lambda gt11 recombinant DNA expression library with a murine monoclonal antibody directed against protein antigens of this pathogen, and b) systematically screening a lambda gt11 genomic cDNA and oligonucleotide probes directed against this pathogen. A 111 kDa protein has been shown to have immunogenic activity against parasite inhibitory antibodies. The gene encoding this protein, including the signal sequence and regulatory sequence in the adjacent 5' flanking sequence has been isolated and sequenced.

Isolation and characterization of genes encoding major protein antigens of *P. falciparum* make it possible to develop reagents useful in the diagnosis, prevention and treatment of malaria. In addition, the signal sequences or regulatory sequences of this gene can be used to stimulate the production of other useful genetic products.

5 Claims, 13 Drawing Sheets

Fig. 2

```
First nt.       10         20         30         40         50         60         70         80         90        100
   +1    AAAATACATA TATTATAACA TAAAGAAAAA TTAAATAAAT CAAACATATT CAAAAAAAAT AAAGTTCTTA AAATATTATA TAACTTAATA CTCATATATC
 +101    AAAAATGAAGT CATATATTTC CTTGTTTTTC ATATTGTGTG TTATATTTAA CAAAAAATGTT ATAAAATGTA CAGGAGAAAG TCAAACAGGT AATACAGGAG
 +201    GAGGTCAAGC AGTAATACA GTAGGAGATC AAGCAGGTAG TACAGGAGGA AGTCCACAAG GTAGTACGGG AGCAAGTCAA CCCGGAAGTT CCGAACCAAG
 +301    CAATCCTGTA AGTTCCGGAC ATTCTGTAAG TACTGTATCA GTATCACAAA CTTCAACTTC CAGGATACAA TTCAAGTAAA ATCAGCTTTA
 +401    TTAAAAGATT ATATGGGTTT AAAAGTTACT GGTCCATGTA ACGAAAATTT CATAATGTTC TTAGTTCCTC ATATATATAT TGATGTTGAT ACAGAAGATA
 +501    CTAATATCGA ATTAAGAACA ACATTGAAAG TGCAATATCA TTTGAATCAA ACAGTGGTTC ATTAGAAATG AAAAAATATG TAAAACTACC
 +601    ATCAAATGGT ACAACTGGTG AACAAGGTTC AAGTACGGGA ACAGTTAGAG ACAGTAGACA ACCAATTTCA GATTCAAGCT CAAGTTCAAG TTCAAGTTCT
 +701    AGTTCAAGTT CAAGTTCAAG TTCTAGTTCA AGTTCAAGTT TTCTAGTTCA AGTTCTAGTT CAAGTCTTCCT GCTAATGGAC
 +801    CTGATTCCCC TACTGTTAAA CCGCCAAGAA TATATGTGAA ACTGGAAAAA ACTTCAAGTT GGTAGTATAT ATTAAGGAGA ATACATTAAT
 +901    AATTAAAATGG AAGTATACG GAGAAACAAA AGATACTACT AATGGAACAA AAGTTGATGT TTGATAAAGT ATTAAAGAAAC CCCATTTACT
+1001    AGTATACTAA TACATGCGTA TTGCTTTTTA TAAAGAACAT AATGGAACAT ACTTCAAGTT AAGGAAAGTAT TCCAGAACAT TGTGATACCT
+1101    TAGCTTCCAA GAAGATATTG TAAGAACTT CAAAGAAATA TATATGTGAA AAGCTCTTT TGATGAAGAT AAAAAGAAAT TCCAGAAAAA AAAAATGACG
+1201    ATACCTATCT GAAGATATTG TATTAGTAAA AATGTTTAAA ACAAATGAAA ATAATGCTTT CAAAGAAATA AAGCTGAGA CAGAAGATGA AATATAAATT AACAGAAATCT
+1301    ATTGATAAAT TATTAGTAAA AATGTTTAAA ACAAATGAAA ATAAGTAGA AGCAAGCTAT AATCAGAATTA GATAATTGAAG TGATAGTTTG AATTAGAAT
+1401    TAATGAATTA CTGTAGTTTA CTTAAAGACG TAGATACAAC AGTACCTTA GGAATGCAAT TCCGTAATGC AGCTGTATGT ATATTAATA ACTTAAAGAG
+1501    ATTATTAATT TATCATTCAG AAGAAAATAT TAAGATAAAT TAAAATAAAT AAAAATAAAT TCCGTAATGC AGCTGTATGT TTGATGATTG GATTGTAAAT
+1601    AAGAGAGGTT TAGTATTACC TGAATTAAAT TATGATTTAG AATATTCCAA TGAACATTTA TATAATGATA AAAATTCTCC AGAAGATAAA GATAATAAAG
+1701    GAAAAGGTGT CGTACATGTT GAAAAATAAT GTATATCTAA TAGAAAAAGA TCTTCAAGTT GAAGATCAAG CTCTTTATGT TCATATGATA ACTCAGAATGA TATGTTTTGT AATAAAGAAT ATTGTAACAG
+1801    ATTAAAAGAT GAAACTGGTA AAGCCTACC GTATATCTAA AAAATTTCTG CAAGATCAAG CTCTTTATGT CTACCAGCA GAATCAAATT TACTTCATGG ATTTTTGCTT CAAAATATCA TTTAGAAACT
+1901    ATTAGATGTA TGAAAGGATA TGAACCTACC ATTATTGAAG ATTATGGATT CTTACCAGCA GAATCAAATT ACAAAAAATGT AACATAAAGA TAGATGTGAT GAAGGTTCTA
+2001    GTCCAATGGA ATTCTTACAA ATTATTGAAG ATTATGGATT TAATGAAAAA ACAAAAAATGA TGAAGTAATG GTTGGAGAAC AATGTCCAAA
+2101    GGTAGAAGAT CACTGGATGA ATCTATGGGA ATCTTACATA TTATTTAAAA TTTGTTAAAA TGAAGTAATG ATCCATAATAG TTAGATGGTA AGGGATATAC TGCATATGAA
+2201    AGTATATGAA TTCATGATAA TATGGATTGCA TATGGATTGCA TTTGTTAAAA TGAAGTAATG GATACAGCTG CAGTATTGAA ATATTATAAA GCTGAAAATG
+2301    TTATGGGATA TGAATTTAGT GGAAAGAAAA TACAGAACTT ATGTGGTGAT GATACAGCTG ATCATGCAGT ATCATGCAGT TAATATTGTT GGTTATGGTA ATTATGTGAA
+2401    TAGCGAAGGA GAAAAAAAAT CCTAATTGGAT TGTAAGAAAC AGTTGGGGGTC CATATTGGGG AGATGAAGGT TATTTTAAAG TATATATGTA TGGACCAACT
```

```
+2501  CATTGTCATT TTAACTTTAT TCACAGTGTT GTTATATTCA ATGTTGATTT ACCTATGAAT AATAAAACAA CTAAAAAAGA ATCAAAAATA TATGATTATT
+2601  ATTAAAGGC  CTCTCCAGAA TTTTATCATA ACCTTTACTT TAAGAATTTT AATGTTGGTA AGAAAAATTT ATTCTCTGAA AAGGAAGATA ATGAAAACAA
+2701  CAAAAATTA  GGTAACAACT ATATTATATT CGGTCAAGAT CAGGACAAAG ACGAATACTG AGCAATACTG CATTAGAATC TGCAGGAACT
+2801  TCAAATGAAG TCTCAGAACG TGTTCATGTT TATCACATAT TAAAACATAT AAAGATAAGAA TGGGTATGCG TAAATATATA GATACACAAG
+2901  ATGTAAATAA GAAACATTCT TGTACAAGAT CCTATGCATT TAATCCAGAG AATTATGAAA AATGTGTAAA TTTATGTAAT GTGAACTGGA AAACATGCGA
+3001  GGAAAAAACA TCACCAGGAC TTTGTTTATC CAAATTGGAT ACAAATAACG AATGTTATTT CTGTTATGTA TAAATAATA TAACAAAAAA AAAAAAAAAA
+3101  AAAAAAA
```

Fig. 2 (continued)

```
MKSYISLFFI LCVIFNKNVI KCTGESQTGN TGGGQAGNTV GDQAGSTGGS
PQGSTGASQP GSSEPSNPVS SGHSVSTVSV SQTSTSSEKQ DTIQVKSALL
KDYMGLKVTG PCNENFIMFL VPHIYIDVDT EDTNIELRTT LKETNNAISF
ESNSGSLEKK KYVKLPSNGT TGEQGSSTGT VRGDTEPISD SSSSSSSSSS
SSSSSSSSSS SSSSSSSSSS SSSSSESLPA NGPDSPTVKP PRNLQNICET
GKNFKLVVYI KENTLIIKWK VYGETKDTTE NNKVDVRKYL INEKETPFTS
ILIHAYKEHN GTNLIESKNY ALGSDIPEKC DTLASNCFLS GNFNIEKCFQ
CALLVEKENK NDVCYKYLSE DIVSNFKEIK AETEDDDEDD YTEYKLTESI
DNILVKMFKT NENNDKSELI KLEEVDDSLK LELMNYCSLL KDVDTTGTLD
NYGMGNEMDI FNNLKRLLIY HSEENINTLK NKFRNAAVCL KNVDDWIVNK
RGLVLPELNY DLEYFNEHLY NDKNSPEDKD NKGKGVVHVD TTLEKEDTLS
YDNSDNMFCN KEYCNRLKDE NNCISNLQVE DQGNCDTSWI FASKYHLETI
RCMKGYEPTK ISALYVANCY KGEHKDRCDE GSSPMEFLQI IEDYGFLPAE
SNYPYNYVKV GEQCPKVEDH WMNLWDNGKI LHNKNEPNSL DGKGYTAYES
ERFHDNMDAF VKIIKTEVMN KGSVIAYIKA ENVMGYEFSG KKVQNLCGDD
TADHAVNIVG YGNYVNSEGE KKSYWIVRNS WGPYWGDEGY FKVDMYGPTH
CHFNFIHSVV IFNVDLPMNN KTTKKESKIY DYYLKASPEF YHNLYFKNFN
VGKKNLFSEK EDNENNKKLG NNYIIFGQDT AGSGQSGKES NTALESAGTS
NEVSERVHVY HILKHIKDGK IRMGMRKYID TQDVNKKHSC TRSYAFNPEN
YEKCVNLCNV NWKTCEEKTS PGLCLSKLDT NNECYFCYV*
```

```
GTAAAATATAATTATTATATAATAAATATATAATAATATTTTTACGCATACACACAAACATTGTCATTATTTTTTTTAGGTGTATATTAACAAAATGTTATAAAATGTACAGGAGAAA  2640
-------------------------------------------------------------------ysValIlePheAsnLysAsnValIleLysCysThrGlyGluS              26

GTCAAACAGGTAATACAGGAGGAGTCAAGCAGTCAGGAGATCAAGCAGGAGTAGTACAGGAGGAAGTCCACAAGGTAGTACAGGGAGCAAGTCAACCCGGAAGTTCCGAACCAA  2760
erGlnThrGlyAsnThrGlyGlyGlyGlnAlaGlySerThrGlyGlyAspThrValGlyAsnThrValGlyAlaGlySerThrGlyAlaSerGlnProGlySerSerGluProS     66

GCAATCCTGTAAGTTCCGGACATTCTGTAAGTACTGTATCAGTATCACAAGTCTTCAGAAAAACAGGATACAAATTCAAGTAAAATCAGCTTTATTAAAGATTATATGGGTT  2880
erAsnProValSerSerGlyHisSerSerGlyValSerThrValSerSerGlnThrSerThrSerSerGluLysSerGlnAspThrIleGlnValLysSerAlaLeuLeuLysAspTyrMetGlyL  106

TAAAAGTTACTACTGGTCCATGTAACGAAAATTTCATATGTTCTTAGTTCCTCATATATATTGATACAGAAGATACTAATATCGAATTAAGAACACATTGAAAGAAACAAATA  3000
euLysValThrGlyProCysAsnGluAsnPheIleMetPheLeuValProHisIleTyrIleAspThrGluAspThrAsnIleGluLeuArgThrThrLeuLysGluThrAsnA  146

ATGCAATAATCATTTGAATCAAACAGTGGTTCATTAGAAAAAAAAATGTAAAACTACCATCAAAATGTGGTGAACAAGGTTCAAGTCGGGAACAGTTACAGGAGATACAG  3120
snAlaIleSerPheGluSerAsnSerGlySerLeuGluLysGluLysLysTyrValLysLeuProSerAsnGlyThrThrGlyValThrGlySerThrGlyThrValArgGlyAspThrG  186

AACCAATTTCAGATTCAATCAAGTTCAAGTTCAAGTTCTAGTTCAAGTTCAAGTTCTAGTTCAAGTTCAAGTTCAAGTTCAGTTCAAGTTCAG  3240
luProIleSerAspSerSerSerSerSerSerSerSerSerSerSerSerSerSerSerSerSerSerSerSerSerSerSerSerSerG  226

AAAGTCTTCCTGCTAATGACCTCATTCCCTACTGTAAACCGCCAAGAATTACAAAATATGTGAAAAAAACTTCAAGTTGGTAGTATATATTAAGGAGAATACATTAA  3360
luSerLeuProAlaAsnGlyProAspSerProThrValLysProProArgAsnLeuGlnAsnIleCysGluThrGlyLysAsnPheLysLeuValValTyrIleLysGluAsnThrLeuI  266

TAATTAAATGAAAGTATACGGAGAAACAAAAGATACTGAAAGTATAAAAAAATAATAAACCGAATAAAAACAATAATAATAATACTTTTTTCTTTTTTTGATTATTTATATTTCAT  3480
leIleLysTrpLysValTyrGlyValThrGlyGluThrGlyLysAspThrThrGluA                                                            281

AAGAAAATGTCATTATACATACAACTACTACTATCAATTTGTTATTATTTATTATTATTATTATTATTATTATTTAGATAACAAAGTTGATGTAACA  3600
-----------------------------------------------snAsnLysValAspValArg                                                  287
```

```
GGATTCTTACCAGCAGAATCAAATTATCCATATAACTATGTGAAAGTTGGAGAACAATGTCCAAAGTAGAAGATCACTGGATGAATCTATGGGATAATGGAAAAATCTTACATAACAAA  4920
GlyPheLeuProAlaGluSerAsnTyrProTyrAsnTyrValLysValGlyGluGlnCysProLysValGluAspHisTrpMetAsnLeuTrpAspAsnGlyLysIleLeuHisAsnLys  684

AATGAACCTAATAGTTTAGATGGTAAGGGATAACTGCATATGAAACTGAAAGATTTCATGATAATATGGATGCATTTGTTAAAATTATTAAAACTGAAGTAATGAATAAAGGTTCAGTT  5040
AsnGluProAsnSerLeuAspGlyLysGlyTyrThrAlaTyrGluLysPheHisAspAsnMetAspAlaPheValLysIleIleLysThrGluValMetAsnLysGlySerVal  724

ATTGCATATATAAAGCTGAAAATGTTATGGGATATGAATTAGTGGAAAGAACTATGTGGTGATGATGCAGTTAATATTGGTTATGGTAATTAT  5160
IleAlaTyrIleLysGluAsnValMetGlyTyrGluPheSerGlyLysLysValGlnAsnLeuCysGlyLysValGlyAspAspThrAlaAspHisAlaValAsnIleValGlyTyrGlyAsnTyr  764

GTGAATAGCCAAGGAGAAAAAAAATCCTATTGAATTGTAAGAACAGTTGGGTCCATATTGGGAGATGAAGGTTATTTAAAGTAGATATGTATGGACCAACTCATTGTCATTTAAC  5280
ValAsnSerGluGlyGluLysGlyLysSerTyrTrpIleValArgAsnSerTrpGlyProTyrTrpGlyValGlyTyrPheLysValAspMetTyrGlyProThrHisCysHisPheAsn  804

TTTTATTCACAGTGTTGTTATATTCAATGTTGATTTACCTATGAATAATAAAAAGAATCAAAAATATATGATTATTAAAGGCCTCTCCAGAATTTATCATAACCTT  5400
PheIleHisSerValValIlePheAsnValAspLeuProMetAsnLysThrThrLysIleSerLysIleTyrAspTyrTyrLeuLysAlaSerProGluPheTyrHisAsnLeu  844

TACTTTAAGAATTTTAATGTTGGTAAGAAAAATTATTCTCTGAAAGGAAGATAATGAAAACATATAATTAGGTAACAACTATATTATATTCGTCAAGATACGGCAGGATCAGGA  5520
TyrPheLysAsnPheAsnValGlyLysLysAsnLeuPheSerGluLysGlyLysAsnTyrIleIlePheGlyAsnAspThrAlaGlySerGly  884

CAAAGTGGAAAGGAAAGCAATACTCCATTAGAATCTCGAGAACTCAAATGAAGTCTCAGAACTGTTCATGTTAAACATATAAAATGTGTAAATTTATCTAATGTGAACTGGAAAACA  5640
GlnSerGlyLysGlySerAsnThrAlaLeuGluSerGluValSerGluArgValHisValTyrHisIleLeuLysAspGlyLysIleArgMetGly  924

ATGCGTAAATATATAGATACACAAGATGTAAATAACAACATTCTGTACAAGATCATTTAATCACAAGAATATGAAAAATGTGTAAATTTATCATGTGAACTGAAAACA  5760
MetArgLysTyrIleAspThrGlnAspValAsnLysLysHisSerCysThrSerArgSerTyrAlaPheAsnProGluAsnTyrGluLysCysAsnValAsnLeuCysAsnValAsnTrpLysThr  964

TGCGAGCAAAAAACATCACCAGGACTTGTTTATCCAAATGGATACAAATAACGAATGTATTCTGTATGTATAAAATATATAACAAAAAAAAAAAAATATTTTTTTAT  5880
CysGluGluLysThrProGlyLeuValTyrProLysGlyTyrAlaAsnGluCysTyrPheCysTyrVal***  989

GTATCCTTTAATTTTAAATAGGGCATAAACTCTCCATTATTCATTTATTAAGGTAGTAATATCTTTAATTTATCATGTACCTCTATAAATATATAAATTATATTAATTATTATT  60
TTTTTTTAAGAATTATTTTTATTCATGTAAAATATAATTCTCTTTTTTTTTTTTAAAAAAAAATACACGATAGTGTACATTAAAATGTATACATTATTATTAACTCGA  6120
ATTC  6124
```

Fig. 6 (continued)

```
              probe A                                     HinfI
           GGGAACAGTTAGAGGAGATACAG AACCAATTTCA GATTC
                                         ▼
Allele  I:    AACAAGGTT CAAGTAC AAGCTCAAGTTCAA   3150
Allele II:   AACAAAGTTCTAGTTCAAGTTCAAGTTCTA
                  probe B Allele  I:    GTTCAAGTTCTAGTTCAAGTTCAAGTTCAA   3180
Allele II:    GTTCAAATTCTAGTTCAAGTTCAAGTTCAA Allele  I:    GTTCTAGTTCAAGTTCAAGTTCAAGTTCAA   3210
Allele II:    GTTCAAGTTCTAGTTCAAGTTCAAGTTCAA Allele  I:    GTTCTAGTTCAAGTTCAAGTTCAAGTTCAG   3240
Allele II:    GTTCTAGTTCAAGTTCAAGTTCAAGTTCAG
```

Fig. 7

GENE ENCODING PROTEIN ANTIGENS OF *PLASMODIUM FALCIPARUM* AND USES THEREFOR

This application is a continuation of application Ser. No. 07/997,092 filed on Dec. 29, 1992 (now abandoned), which is a divisional of Ser. No. 07/870,806 filed Apr. 17, 1992 (now abandoned), which is a file wrapper continuation of Ser. No. 07/231,771 filed Aug. 12, 1988 (now abandoned).

FUNDING

Work described herein was supported by funding from the National Institutes of Health grant No. AI22038.

BACKGROUND

Malaria is a significant global health problem. It is widespread, and consitutes a growing health problem of major proportions, particularly in developing countries.

Malaria is caused by several species of the genus Plasmodium, the most virulent species being *Plasmodium falciparum* (*P. falciparum*). Parasites growing in erythrocytes are responsible for the pathological manifestations of the disease in man. During the blood stage of infection, *P. falciparum* parasites infect the cells and develop within the erythrocytes through three successive, morphologically distinct stages known as ring, trophozoites and schizonts. A mature schizont eventually produces multiple infectous particles, known as merozoites, which are released upon rupture of the red blood cells. The merozoites invade new red blood cells after a short extracellular life in the blood.

The increased resistance of the malaria parasite to drugs, as well as the resistance of the mosquito vector to insectide, has increased the need for a malaria vaccine. H. S. Banyal and J. Inselburg, *Am. J. Trop. Med. Hyg.*, 34(6): 1055–1064 (1985). One approach to the development of a vaccine has been to use monoclonal antibodies to identify and characterize specific malarial antigens involved in antibody-sensitive processes that are essential to the maintenance of the parasite growth cycle. These antibodies are known as "parasite inhibitory" antibodies. These parasite inhibitory antibodies can be induced by a host's immune response to the complementary antigens. Such an antigen, or combination of antigens, could therefore provide the basis for an effective malarial vaccine. Some parasite inhibitory antibodies have been isolated and the *P. falciparum* parasite antigens they recognize have been identified by H. S. Banyal and J. Inselburg, in *Am.J. Trop. Med. Hyg.*, 34(6):1055–1064 (1985). See also, P. Deplace, et al., *Molecular and Biochemical Parasitology*, 23: 193–201 (1987); J. L. Weber, et al., *Molecular Strategies of Parasitic Invasion*, Agubian, Goodman and Nogueira (Eds.), Alan R. Liss, Inc., New York, N.Y. pp. 379–388 (1987); P. Deplace, et al., *Molecular and Biochemical Parasitology*, 17: 339–251 (1985); J. D. Chulay, et al., *The Journal of Immunology*, 139: 2768–2774 (1987); and A. Bhatia, et al., *Am. J. Trop. Med.*, 36(1): 15–19 (1987).

The key to developing an antimalarial vaccine based on a defined antigen is to isolate and characterize the gene encoding the antigen recognized by a parasite inhibitory antibody so it may be manipulated by gene cloning techniques to provide sufficient amounts of appropriate antigen for vaccine production.

Available approaches to diagnosing, preventing and treating malaria are limited in their effectiveness and must be improved if a solution is to be found for the important public health problem malaria represents worldwide.

SUMMARY OF THE INVENTION

The invention pertains to an isolated nucleic acid sequence which encodes the SERA protein antigen of the malaria parasite *Plasmodium falciparum* (*P. falciparum*), which antigen is capable of eliciting parasite inhibitory antibodies in a parasite host. The term "SERA" is derived from serine repeat antigen based on the presence of a serine repeat sequence in the amino acid sequence of the protein.

In particular, the invention comprises the *P. falciparum* cDNA having the nucleotide sequence shown in FIG. 2, the amino acid sequence derived from it shown in FIG. 3, and the genomic DNA sequence shown in FIG. 6. The isolated genomic DNA sequence of the invention can include the SERA gene regulatory sequences contained in the 5' flanking sequence of the gene, and the signal sequences, also shown in FIG. 3 and FIG. 6. The regulatory sequences can be used to direct expression of the SERA gene, or they may be used independent of the SERA DNA sequences, to direct the expression of other DNA sequences, especially other malarial DNA sequences. The signal sequences can be used to direct exportation of the SERA protein, or independent of the SERA DNA, to direct exportation of a protein by a cell.

The invention also pertains to the immunogenic protein antigen, SERA, or immunogenic equivalents thereof, encoded by the isolated DNA of the invention. The amino acid sequence of the protein antigen is shown in FIG. 3 and FIG. 6. The protein can be produced by recombinant DNA techniques. For example, cDNA of the invention can be incorporated into an expression vector and the vector used to infect a host cell for expression of the SERA antigen.

This invention includes a malaria vaccine which is composed of the SERA antigen or a portion thereof, in a pharmaceutically acceptable carrier, and a method of vaccinating against malaria with this vaccine.

BRIEF DESCRIPTION OF THE FIGURES

FIG. 2 shows the cDNA sequence encoding the SERA protein. The sequence begins in the non-translated leader sequence for the SERA gene mRNA.

FIG. 3 shows the amino acid sequence of the SERA protein. The 989 amino acids encoded by the SERA gene are shown using the one letter code. The signal sequence and the three possible N-linked glycosylation sites of the SERA gene are underlined.

FIG. 6 shows the genomic DNA sequence of the SERA gene and the amino acid sequence which it encodes. Nucleotide sequences corresponding to the broken line of the amino acid sequence indicates the location of the three SERA gene introns. The stop codon is marked ***. Several restriction sites are boxed: three HinfI sites, GANTC, and one EcoRI site, GAATTC. The 5' nucleotide of the clone MBN#3102 is underlined (T, nucleotide 3795). The regulatory sequence is encoded by base pairs 485–2526.

FIG. 7 shows portions of the SERA allele I and allele II repeat sequences, AG(T or C) TC(A or T), encoding the polyserine repeats. The nucleotide numbers in the right margin correspond to those in FIG. 6. The upper 39 bp sequence found in allele I at the position shown, is absent from allele II. Eight single nucleotide differences between allele I and allele II were underlined in allele II. A ninth nucleotide change in the coding region is not shown (nucleotide 3993 in Table I). The two boxed sequences shown were chosen to make the oligonucleotide probes (probe A in cDNA to identify allele I and probe B in clone E31 genomic DNA to identify allele II). A HinfI restriction site in the 39 bp sequence is also boxed.

DETAILED DESCRIPTION OF THE INVENTION

Figure 6:
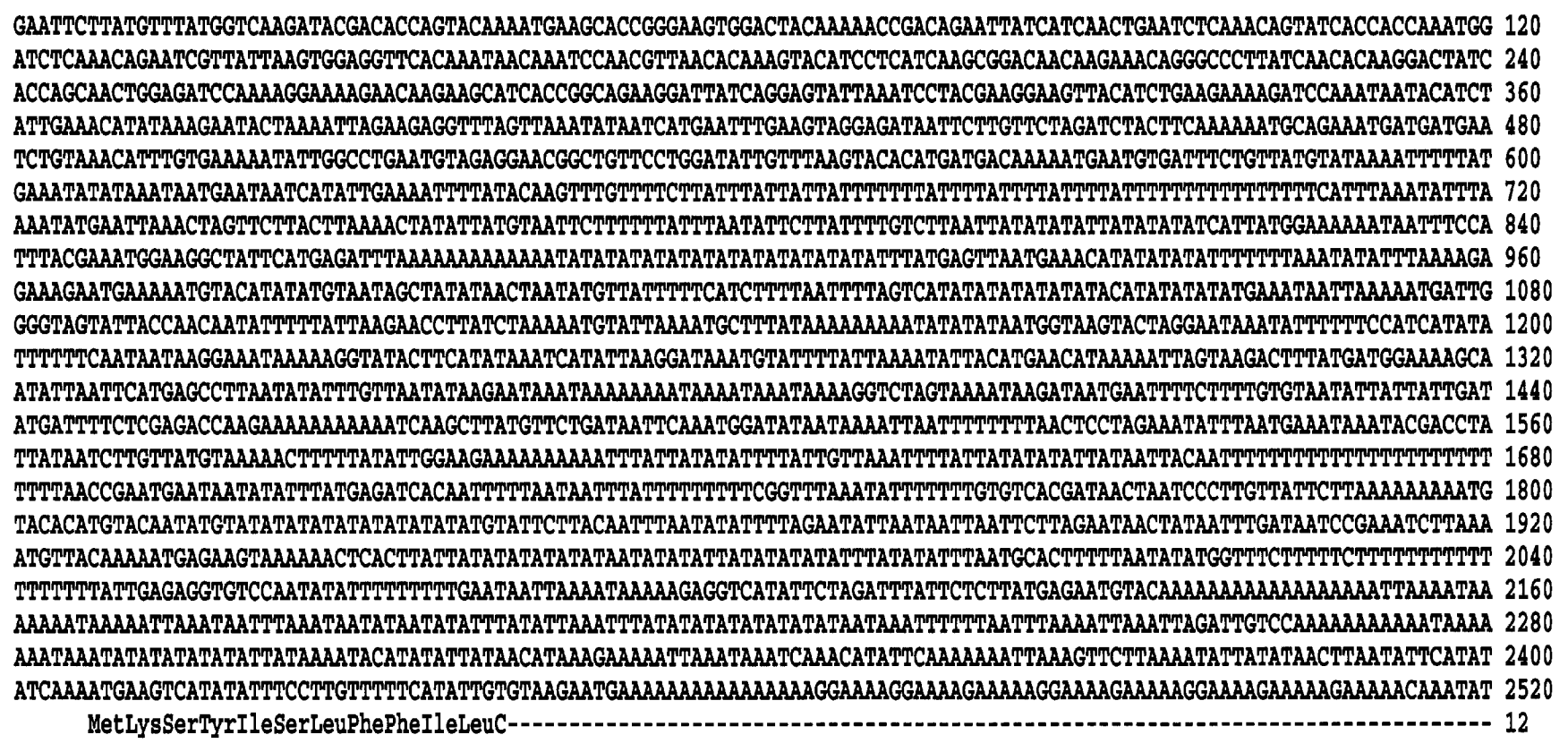
Figure 6:
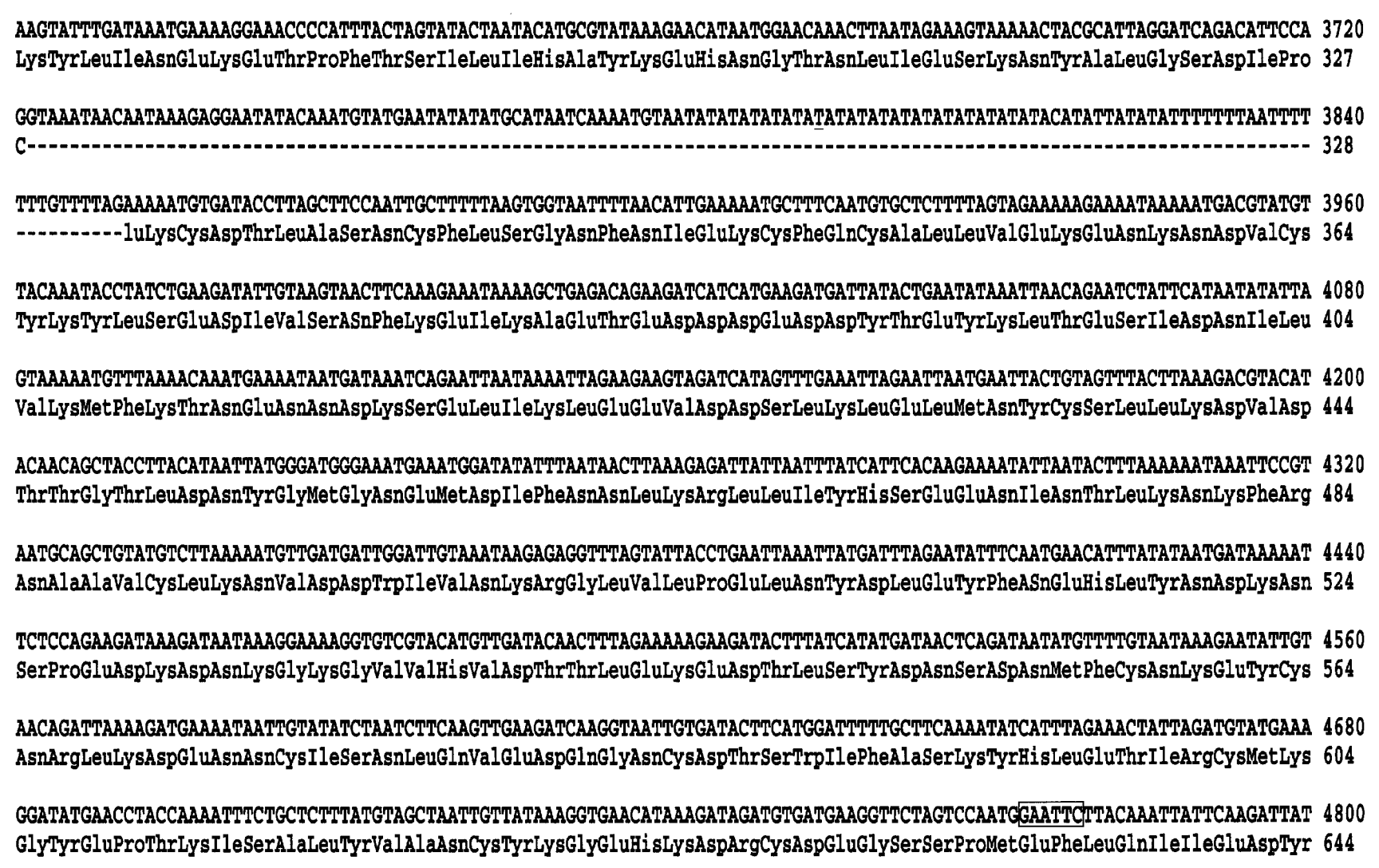

The SERA gene encodes the SERA antigen, which is an immunogenic protein antigen of the parasite *P. falciparum*, the most virulent species of malaria. FIG. 2 shows the nucleotide sequence encoding the SERA antigen. FIG. 3 shows the amino acid sequence derived from that cDNA sequence, and FIG. 6 shows the genomic DNA, introns, and flanking sequences that contain the transcriptional regulatory sites as well as the encoded amino acid sequence. The nucleotide sequence of the invention includes DNA sequences substantially complementary to the nucleotide sequence shown in FIGS. 2 and 6, or portions thereof, including additions, deletions and variations of the nucleotide sequence which encode one or more antigenic determinants of the SERA antigen.

Figure 1:
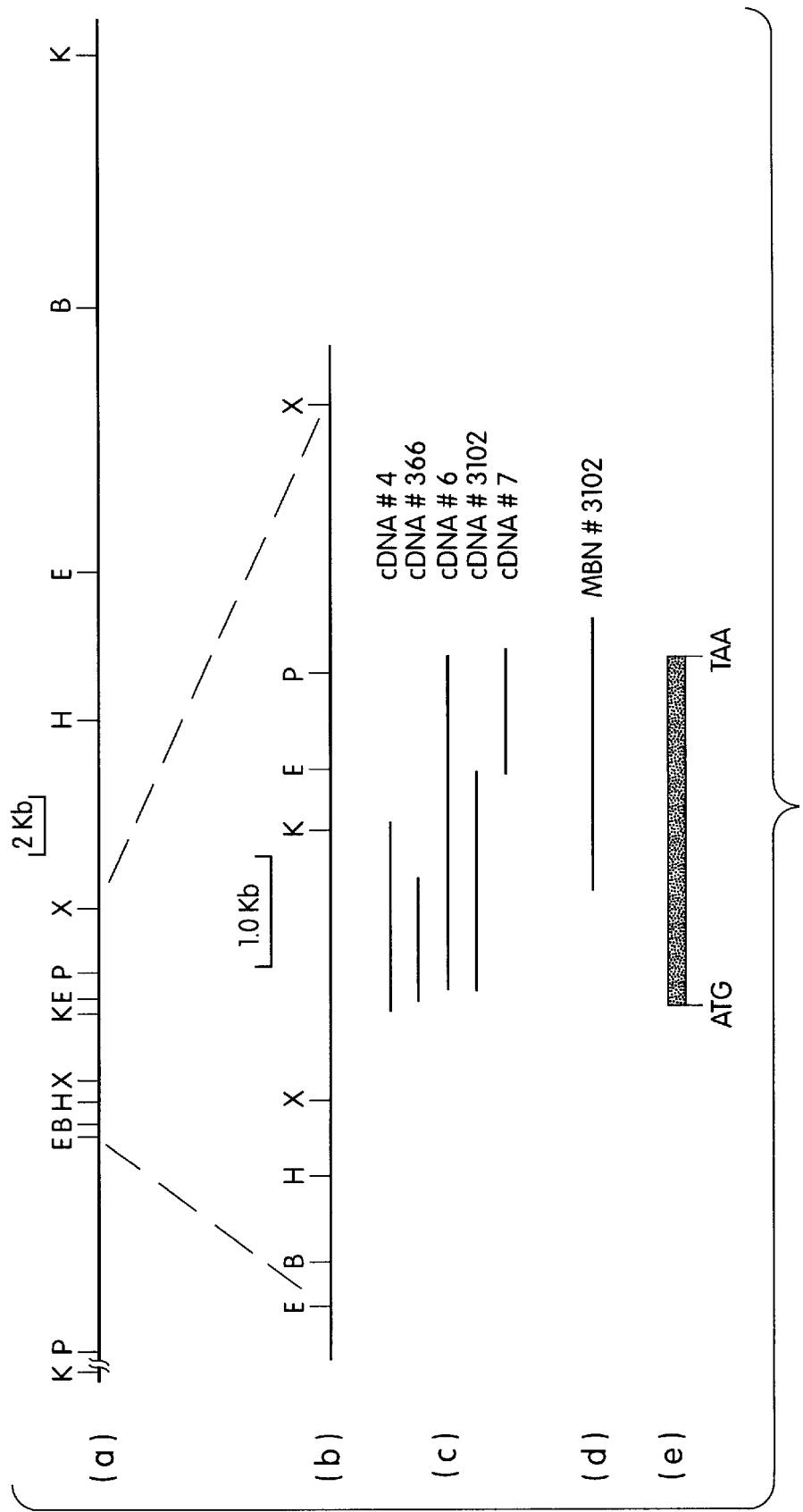
FIG. 1 shows a schematic representation of the restriction map, cDNA and genomic clones for the SERA gene. (a) Restriction sites shown are B. BglII; E. EcoRI; H. HindIII; K. KpnI; P. PstI; X. XbaI. (b) Enlarged restriction map encompassing the SERA gene. (c) Locations of certain cDNA molecules. (d) Location of the genomic DNA clone MBN#3102. (e) Location of the long open reading frame coding for the SERA protein.

The SERA gene was isolated from the *P. falciparum* genome using recombinant DNA techniques. Briefly, RNA was obtained from red blood cells containing parasites in the trophozoite and schizont stages. A lambda gt11 expression library was constructed from the RNA, and the expression library was screened immunologically with pooled human immune serum to form a gene bank of positive clones. The gene bank expressed antigens recognized by human antimalarial polyclonal serum. The positive-clone gene bank was then screened with a parasite-inhibitory, mouse monoclonal antibody, 43E5, to identify clones producing antigens recognized by both it and the parasite-inhibitory human antibodies. A cDNA clone in the gene bank, designated clone #366, was isolated. Clone #366 strongly reacted with both the human immune sera and the murine monoclonal antibody, indicating that it encoded an immunogenic protein antigen present in the blood stage of the parasite. The cDNA clone was then sequenced to obtain part of the complete nucleotide sequence shown in FIG. 2. The complete cDNA sequence in FIG. 2 was finally established using clone #366 as a probe of cDNA libraries and other probes developed from clones in such libraries. A representation of the clones derived starting with clone #366, from which the complete cDNA sequence was determined, is shown in FIG. 1.

Figure 5:
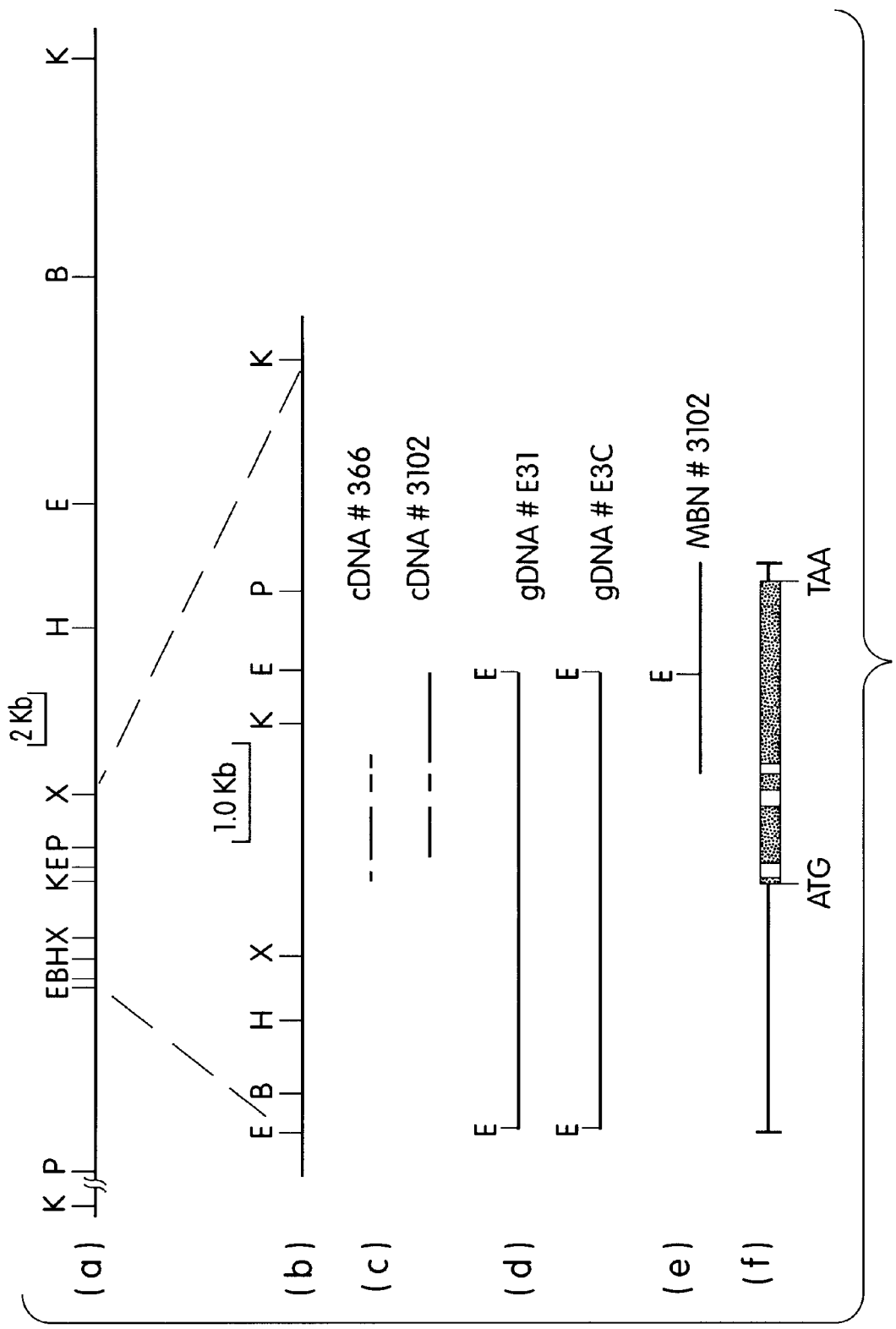
FIG. 5 shows the a schematic representation of the restriction map of the SERA gene, cDNA clones and genomic DNA clones. (a) Restriction sites shown are $B_1$ BglII; E, EcoRI; H, HindIII; K, KpnI; P, PstI; x, XbaI. (b) Enlarged restriction map encompassing the SERA gene. (c) Location of the cDNA clones used as probes in this study. (d) Location of the genomic clones E31 and E3C. (e) Location of the genomic DNA clone MBN#3102. (f) Location of the SERA genomic DNA including the exons, introns and flanking sequences. Three introns are clear (☐) boxes and the exons are filled (■) boxes.

The complete genomic DNA sequence was established using two genomic DNA clones gDNA #E3C and MBN#3102 (see FIG. 5). The genomic sequence with introns is shown in FIG. 6.

The gross protein structure appeared conserved in 10 geographically separate *P. falciparum* isolates. Bhatia et al., *Am. J. Trop. Med. Hyg.*, 36:15–19 (1987). The independent demonstration of its parasite-inhibitory immunogenicity, its abundance in late developmental stages, its accessibility to the host immune system, and its apparent conservation in geographically isolated strains all suggest the antigen is an excellent candidate antigen for a vaccine. The knowledge of the complete SERA sequence and genomic structure, which is essential for the engineering of its production, makes its use as a vaccine practical.

A vaccine based on the SERA protein, or an immunogenic portion of the protein, can be made by incorporating the protein into a pharmaceutically acceptable carrier. For example, the SERA antigen or portions thereof containing one or more antigenic determinants of the SERA antigen can be prepared in injectable form for parenteral administration by incorporating them in a vehicle with or without an adjuvant.

The protein antigens encoded by part of or the entire SERA gene of *P. falciparum* may be used in serodiagnostic tests for malaria. Such antigens would be highly specific to *P. falciparum*, and the tests in which they are used would also be highly specific. Highly specific serological tests would be of great value in screening populations for individuals producing antibodies to *P. falciparum*; in monitoring the development of active disease in individuals, and in assessing the efficacy of treatment. As a result of using such a diagnostic tool, early diagnosis of malaria will be feasible, thus making it possible to institute treatment at an early stage in the disease and, in turn, reduce the likelihood it will be transmitted.

The cDNA nucleotide sequence of the SERA gene, (shown in FIG. 2), the amino acid sequence and the genomic sequence of the SERA gene (both shown in FIG. 6), have been identified. Recombinant DNA techniques can be used to produce the SERA protein. In these techniques, generally, the DNA encoding all or a desired part of the protein would be incorporated into a DNA expression vector, such as a plasmid. The resulting recombinant vector can then be introduced into a host cell. Generally the host cell is a prokaryote, such as *E. coli*, but eukaryotic host cells can be employed. The transformed cells can be screened for the production of the gene product. This can be accomplished by linking the DNA of interest to a marker gene in the vector, such as LacZ, or by direct assay, such as by using antibodies to detect the presence of the antigen. The cells which are found to express the antigen at high levels can then be cultivated to produce desired quantities of the protein.

The region of the genomic DNA containing gene regulatory sequences associated with the SERA gene (shown in FIG. 6, bp 485–2526) cause the SERA gene product to be produced at very high levels in the parasite. Based on a Northern blot analysis of trophozoite and schizont mRNA and an analysis of the *P. falciparum* cDNA library with SERA gene probes, as much as 2% of trophozoite and schizont mRNA is devoted to this antigen's production (see FIG. 4). The regulatory sequence of the SERA DNA can be used to stimulate high-efficiency expression of other genes in addition to the SERA gene. For example, the regulatory sequences can be isolated using the appropriate restriction endonucleases, or it can be synthesized. The regulatory sequence can then be incorporated into a vector, such as a plasmid, to direct the expression of a gene of choice.

The SERA signal sequence (shown in FIG. 3, in one letter code for amino acids, as the amino acid sequence MKSYISLFFILCVIFN) can be used to cause the SERA protein, or other proteins to which it becomes linked, to be exported. The SERA signal sequences can be linked to a protein-encoding DNA sequence to produce secretable protein. The signal sequence directs the passage of the protein through the cell membrane. Such signal or "pre" sequences are characteristic of secreted proteins and consist mainly of hydrophobic amino acid residues which determine the export of the protein across the cell membrane. The SERA signal sequence can be incorporated into a vector with the gene of choice, with an appropriate flanking promoter sequence. Normally the signal sequence is placed upstream of and adjacent to the gene. The vector is then used to transform a host cell. The recombinant host cell will secrete the protein encoded by the gene of choice as directed by the SERA signal sequence.

The invention is further illustrated by the following exemplification.

EXEMPLIFICATION
MATERIALS AND METHODS

Parasites and Culture Conditions

*P. falciparum* strains FCR3 and Honduras I were grown in vitro as described by W. Trager and Jensen in *Science*, 193:673–675 (1976) and by J. Inselburg, *J. Parasitol*, 69:584–591 (1983). RPMI 1640 medium was supplemented with 25 mM HEPES buffer (pH 7.2), 0.2% sodium bicarbonate, 10% heat inactivated human plasma (type A, Rh$^+$), penicillin (100 IU ml$^{-1}$), streptomycin (100 µg ml$^{-1}$), and gentamycin (20 µg ml$^{-1}$).

Synchronization of parasites was done by the sorbital method, C. Lambros and S. P. Vandenburg, *J. Parasitol.*, 65:418–420 (1976), and a population of trophozoite and schizont containing red blood cells (RBC) was prepared by Plasmagel fractionation of a culture. R. T. Reese, et al., (1979) B711.WHO57 (suppl.), 53–61.

Preparation of Parasite RNA and DNA

Red blood cells (RBCs) containing parasites in the trophozoite and schizont stages were washed once with RPMI 1640 medium, resuspended in a solution that contained 0.015% saponin, incubated for 0.3 hours at 37° C., and were then collected and washed twice by centrifugation with phosphate buffered saline (PBS 0.01 M $KH_2PO_4/NaHPO_4$, 0.14 M NaCl, pH 7.4).

Total parasite RNA was isolated using the guanidium isothiocynate method. The Poly(A) RNA was purified through an oligo d(T)-cellulose column as described previously. T. Maniatis, et al., *Molecular Cloning: A Laboratory Manual*, Cold Spring Harbor Laboratory, Cold Spring Harbor, N.Y. (1982).

Chromosomal DNA was co-purified with the RNA from the GUITC homogenate. After ultracentrifugation of the GuITC homogenate, the DNA on the CsCl shelf was collected and purified by conventional CsCl banding (T. Maniatis, et al., ibid.)

Construction of a cDNA Expression Library

The method of cDNA synthesis using reverse transcriptase and the Klenow fragment of *Eschericia Coli* DNA polymerase I was followed. T. Maniatis, et al, ibid. Ten micrograms of poly(A) RNA was used in each reaction. After the synthesis of the second strand, the cDNA hairpin structure was cut with S1 nuclease (Bethesda Research Labs), and the reaction was treated with a phenol/chloroform mixture. The purified double stranded cDNA was repaired by successive treatment with the Klenow fragment of DNA polymerase I and T4 DNA polymerase (New England Biolabs). The DNA was methylated with EcoRI methylase and the cDNA was ligated with an octamer EcoRI linker (GGAATTCC). After digestion with EcoRI, the DNA was fractionated by size using agarose gel electrophoresis to avoid possible bias in the size distribution of the cDNA library. The cDNAs with the length of 0.2–0.5 kb, 0.5–2 kb, 2–5 kb and 5–10 kb were separately collected by electrophoresis onto DEAE 81 paper. G. Dretzen, et al., *Anal. Biochem.*, 112:295–298 (1981). The lambda gt11 phage (R. A. Young and R. W. Davis, *Proc. Natl. Acad. Sci. USA*, 80:1194–1198 (1983)), was the vector used for construction of the cDNA expression library. (T. Maniatis et al., ibid.)

Mung Bean Nuclease Genomic DNA Libraries

Mung bean nuclease (MBN) digestion of FCR3 parasite DNA was done as described by D. J. Bzik et al. in *Proc. Nat'l. Acad. Sci. USA*, 84:8360–8364 (1987). DNA fragment sizes of 0.75 to 3.0 kb and 3.0 to 10 kb were collected from a 1.0% agarose gel and purified. The libraries were constructed in the lambda phage vector lambda gt11, as for the cDNA library above.

Construction and Screening of Genomic DNA Libraries

Genomic DNA libraries were constructed in lambda gt11 as an EcoRI library (G. Dretzen et al., (1981) *Anal. Biochem.*, 112:295–298) and as an MBN library. Gene fragments in lambda gt11 were subcloned into the plasmid pUC19 and the recombinant plasmids were introduced into *E. coli* strain DH5 by transformation. D. Hanahan, *J. Mol. Biol.*, 166:557–580 (1983). Plasmid DNA was prepared exactly as previously described. T. Maniatis et al., ibid.

Screening of Recombinant Phage by Immunochemical Reactions

Phage producing parasite antigens were screened by an in situ plaque immunoassay. R. A. Young and R. W. Davis, *Proc. Nat'l Acad. Sci. USA*, 80: 1194–1198 (1983). About 100,000 packaged phage were screened. The source of antimalarial polyclonal antibody was pooled Nigerian serum provided by Dr. D. Haynes (Walter Reed Army Institute of Research). The Nigerian serum was used at a 1:200 dilution. In total, 288 of the screened Nigerian positive phages were collected, and represented clones from each size fraction of the cDNA library.

Oligonucleotide Synthesis and Labeling

Two single stranded SERA gene specific oligonucleotides, called probe A (a 30-mer: 5'CTG TAT CTC CTC TAA CTG TTC CCG TAC TTG 3') and probe B (a 31-mer: 5'CTA GAA CTT GAA CTT GAA CTA GAA CTT TGT T 3') were synthesized at the Dartmouth Molecular Genetics Center, Hanover, N.H. The oligonucleotides were purified on polyacrylamide gels and end-labeled using $T_4$ polynucleotide kinase and ($^{32}$P) ATP. T. Maniatis et al., ibid.

Subcloning of the cDNA Inserts

DNA from positive phage clones identified in the previous section were purified and subcloned into plasmid pUC19 at its EcoRI site. T. Maniatis et al., ibid. A pUC19 plasmid cloning vector was linearized by EcoRI digestion and treated with calf intestinal phosphatase. One microgram of a phage clone DNA was cleaved with EcoRI, extracted with phenol/chloroform, ethanol precipitated, and mixed with 0.5 ug of the prepared plasmid DNA in 25 ul of ligation mixture. *E. coli* HB101 or DA52 competent cells (Bethesda Research Labs) were transformed with the ligated DNA by the procedure described by the manufacturer and plated on ampicillin (100 $\mu$g ml$^{-1}$) containing LB plates.

In situ and Southern Hybridization

Phage DNA was transferred to nitrocellulose. T. Maniatis et al., ibid. Restriction enzyme digested *P. falciparum* DNA was transferred to Zeta probe membranes (BioRad, Richmond, Calif.) using the alkaline transfer method as previously described. K. C. Reed and D. A. Mann, *Nucleic Acids Res.*, 13:72077221 (1985) and J. Inselburg et al., *Mol. Biochem. Parasitol.*, 26:121–134 (1987). A. P. Feinberg and B. Vogelstein, *Anal. Biochem.*, 32:6–13 (1983) and *Anal. Biochem.*, 137:266–267 (1984). Typically, 50 ng of DNA to be used as a probe was oligo-labelled to a specific activity of 1 to 3×10$^9$ cpm $\mu$g$^{-1}$ of DNA. Hybridization conditions were identical for plaque lifts and Southern blots. Hybridizations were usually done overnight at 42° C., in 35% formamide (vol/vol), 6×SSC (T. Maniatis et al.), 0.5% BLOTTO (D. A. Johnson et al., (1984) *Gene Anal. Tech.*, 1:3–8 and 5 $\mu$g poly(A) ml$^{-1}$. The addition of exogenous poly(A) dramatically decreased background hybridization. After hybridization, filters were washed 3 times, for a total of 0.5 h in 1×SSC and 0.1% sodiumdodecylsulfate (NaDodSO$_4$) at room temperature. The filters were then washed twice for 1 hour at 60° C., or more, in 1×SSC and 0.1% NaDodSO$_4$ to remove non-specific hybridizing material.

Northern Blot Analysis

Total *P. falciparum* RNA and poly(A)$^+$ RNA were prepared as previously described. Total RNA and poly(A)$^+$ RNA of malaria were size-fractionated by electrophoresis in a 1.2% agarose formaldehyde (6.7%) gel (Lehrach et al., *Biochemistry*, 16:4743–4751 (1977) and then electrophoretically blotted onto Zetabind membrane (CUNO, Inc. Meriden, Conn.). Hybridization of $^{32}$P-labeled cDNA to RNA-containing filters was done overnight at 42° C. Wahl, et al., *Proc. Nat'l. Head. Sci. USA*, 76:3683–3687 (1979). Hybridization of probe A and probe B oligonucleotides to the RNA-containing filters was done by treating the filters for 2 hr at 37° C. in a solution containing 1 M NaCl, 1033 Denhardt's solution, 5% NaDodSO$_4$, 10 mg of poly(A) ml$^{-1}$, and 0.1 mM ATP, followed by hybridization overnight at 37° C. in 1 M NaCl, 10×Denhardt's solution, 1% NaDodSO$_4$, 5% formamide, and 10% Dextran sulfate. The filters were then washed in 1 M NaCl, 10×Denhardt's solution and 1% NaDodSO4 for 30 min at 37° C. Finally, the filters were washed, as required, in more stringent conditions.

DNA Sequencing

DNA sequencing was performed as previously described by D. J. Bzik, et al. in *Proc. Nat'l Acad. Sci. USA*, 84:8360–8364 (1987), using the dideoxynucleotide technology. F. Sanger et al., *Proc. Nat'l Acad. Sci. USA*, 74:5463–5467 (1977). Briefly, DNA fragments were purified (G. Dretzen et al., (1981), *Anal. Biochem.*, 112:295–298), self-ligated, and sonicated. P. L. Deininger, *Biochem.*, 129:216–223 (1983). 0.3 to 0.7 kb fragments were purified and the DNA ends were enzymatically repaired (blunted) and cloned into SmaI digested, alkaline phosphatase treated M13mp8. Every bp of the sonicated fragments was independently sequenced approximately 6 times (average), and both DNA strands were completely sequenced. DNA sequences were reconstructed using the DNA Inspector II programs (Textco, West Lebanon, N.H.). The BIONET computer resource for molecular biology (IntelliGenetics, Palo Alto, Calif.) was also utilized to manipulate and to compare DNA and amino acid sequences.

RESULTS

Construction of the Blood Stage cDNA Gene Bank

Parasite poly(A) RNA was prepared from parasites in the late trophozoite and schizont stages to construct a lambda gt11 cDNA expression library. This period of the erythrocytic growth cycle is when both protein and RNA synthesis is most active, and when the greatest numbers of different proteins appear to be synthesized. H. Banyal and J. Inselburg, *Am.J.Trop. Med. Hyg.*, 34: 1055–1064 (1985). The FCR3 cDNA library was screened with a pooled human Nigerian serum that contained antibodies reactive with numerous malaria proteins identified by western blot analysis. About 100,000 packaged phage were screened and 288 positive clones were picked, purified, and numbered to form the FCR3 gene bank that was used to screen other sources of antimalarial antibodies.

Lambda gt11 is a bacteriophage vector which is capable of driving the expression of foreign DNA which is inserted into its genome with *E. coli* transcription and translation signals. Lambda gt11 expresses the insert DNA as a fusion protein connected to the *E. coli* beta-galactosidase polypeptide. This approach ensures that the foreign DNA sequence will be efficiently transcribed and translated in *E. coli*. This approach is also useful in addressing the problem of the highly unstable nature of most foreign proteins; fusion proteins are often more resistant to proteolytic degradation than the foreign polypeptide alone. The use of lambda gt11 and the *P. falciparum* strains used (FCR3 and Honduras-1) are described by T. Horii, D. J. Bzik and J. Inselburg in *Molecular and Biochemical Parasitology*, 30:9–18 (1988). The teachings of this publication are incorporated herein by reference.

Determining the Structure of the SERA cDNA

Clone cDNA #366 reacted more strongly with mMAb 43E5, so this clone was selected for further study. The cDNA #366 was subcloned into-pUC19.

The frequencies of expression of the genes coding for cDNA #366 were estimated by using the oligo-labelled cDNA #366 sequence as a probe of the original cDNA library. Ten thousand phage plaques from the library were assayed by in situ DNA hybridization with each probe. 1.5% of total cDNA phage containing inserts were hybridizable with the cDNA #366.

Isolation of SERA cDNA Clones and a Genomic DNA Clone cDNA#366 DNA was used as a probe to select additional cDNA clones from a cDNA library by DNA hybridization. Five additional cDNA clones that hybridized with radioactively labeled cDNA#366 DNA were isolated, purified, and analyzed. Each of those five cDNA clones contained a single EcoRI fragment insert. The largest clone, cDNA#3102, contained a 1.8 kb EcoRI insert. The cDNA#3102 DNA sequence did not contain a poly(A) sequence. The DNA sequences of cDNA#366 and cDNA#3102 had a 971 bp overlap and together they encoded a 629 amino acid sequence of the SERA gene.

In order to obtain the 3' cDNA sequences a MBN genomic DNA library was constructed and screened to identify both the 3' cDNA and 5' cDNA containing clones of the SERA gene, because MBN was previously shown to cleave near, but outside of, P. falciparum coding regions. Radioactively labeled cDNA#3102 was used to screen the genomic MBN libraries (0.75 to 3.0 kb; and 3.0 to 10 kb size fractions). 100,000 phage from each library were screened and one clone, MBN#3102, from the 0.75 to 3.0 kb MBN library, hybridized with cDNA#3102. The MBN#3102 clone contained two EcoRI fragments, of 1.0 kb and 1.4 kb. The 1.0 kb EcoRI fragment strongly hybridized with cDNA#3102 sequences. The 1.4 kb EcoRI fragment hybridized very weakly with cDNA#3102 sequences under low but not high stringency washing conditions. Two approaches were used to determine if the 1.4 kb EcoRI fragment of MBN#3102 contained 3' coding sequences of the SERA gene or represented a random double ligation event. The cDNA libraries were screened by hybridization with either the 1.0 or the 1.4 kb EcoRI fragment of MBN#3102. If both of these fragments were adjacent on chromosomal DNA and represented SERA gene sequences, then many cDNA clones should strongly hybridize with both of them. In cDNA libraries constructed from both the 0.5 to 2.0 kb and the 2.0 to 5.0 kb cDNA fragments, many of the cDNA clones strongly hybridized with both the 1.0 kb and 1.4 kb EcoRI fragments. In the second approach, the hybridization pattern of both the 1.0 kb and 1.4 kb EcoRI fragments in Southern blotting experiments were analyzed.

In Southern blotting experiments of parasite genomic DNA it was observed that the 1.0 kb and 1.4 kb EcoRI fragments of MBN#3102 hybridized to the same major bands in BglII, HindIII, and KpnI digests of chromosomal DNA. It was concluded that the two fragments were adjacent on the chromosomal DNA and did not represent a double-ligation event of random EcoRI fragments. A preliminary restriction map for FCR3 and Honduras-1 DNA, which behaves similarly to FCR3 DNA, was constructed from hybridization data (see FIG. 1).

Nucleotide Sequence of the cDNA Clones and the Amino Acid Sequence of the SERA Gene Additional cDNA clones that hybridized with MBN#3102 DNA sequences were identified. Sixteen of those cDNA clones were selected, plaque purified, and their inserts subcloned into pUC19. Their insert sizes were determined by EcoRI digestion and Southern hybridization with the 1.0 kb and 1.4 kb EcoRI fragment of MBN#3102 (the 3' probe) were all approximately 1.0 to 1.1 kb in size. This indicated the distance from the unique EcoRI site in the SERA gene to the 3' end of the mRNA was about 1.0 to 1.1 kb. Several 5' cDNA clones were selected for DNA sequence analysis. The locations of some of those cDNA clones (FIG. 1c) and the MBN#3102 clone (FIG. 1d) are shown. The alignment of the cDNA clones with the genomic restriction map (FIG. 1b) was based on the presence or absence of the unique KpnI, PstI, and EcoRI sites in the cDNA clones, and upon the aligned DNA sequences of the cDNA clones The DNA sequences for the following cDNA clones: cDNA#4, cDNA#6, cDNA#7, cDNA#366 and cDNA#3102 were determined.

The aggregate cDNA sequence derived from all of those clones is shown in FIG. 2. The complete DNA sequence for both DNA strands was determined for each cDNA clone. Minor differences from the consensus cDNA sequence were found in some cDNA clones and are summarized in Table 1.

TABLE 1

Resolution of Base-pair Differences Between SERA cDNA clones

| cDNA clone | Location[a] | bp difference | Resolution |
|---|---|---|---|
| cDNA#4 | 1 to 1571 | NONE | |
| cDNA#366[b] | 126 to 1183 | bp 233; G to A | G was present in cDNA#4 cDNA#6, and cDNA#3102 |
| | | bp 1169; G to A | G was present in cDNA#4, cDNA#6, and cDNA#3102. |
| | | bp 1175; G to A | G was present in cDNA#4, cDNA#6, and cDNA#3102 |
| | | bp 1180; T to A | T was present in cDNA#4, cDNA#6, and cDNA#3102 |
| cDNA#6 | 168 to 3058 | bp 1738; deleted | A was present to cDNA#3102 |
| | | bp 222; T to G | T was present in cDNA#4, cDNA#366, and cDNA#3102 |
| | | bp 228; A to G | A was present in cDNA#4, cDNA#366, and cDNA#3102 |
| cDNA#3102 | 212 to 2014 | NONE | |
| cDNA#7 | 2009 to 3107 | NONE | |

[a]- bp location numbers are from FIG. 2.
[b]- cDNA#366 sequence is from reference Horii, T., et al., Molec. and Biochem. Parasitol., 30:9–18 (1988).

There were 7 base pair (bp) discrepancies between the total 8,427 bp determined for the cDNA clones, and a bp at these locations was assigned (Table 1). Three of the base differences were located at the 3' end of cDNA#366 and were caused during the second strand synthesis in cDNA construction due to the annealing of an oligo-dT molecule at this site (Table 1). cDNA#6 had a 1 bp deletion (bp 1738), probably generated during either cDNA synthesis or the cloning process. The remaining three base changes were clustered at bp 222, 228, and 233 and may represent mRNA polymorphism based on those changes being located in the degenerate octamer repeat of the SERA gene. The presence of the unique EcoRI site (bp 2009 to 2014) in the gene was confirmed by sequencing across that EcoRI site in the phage DNA for both cDNA#6 and MBN#3102.

A long open reading frame began with the ATG at bp 104 and ended at the TAA at bp 3071 (FIG. 1 and FIG. 2). That reading frame, which encoded the SERA gene, contained 989 amino acids with a predicted molecular mass of 111 kDa (FIG. 3). The SERA gene amino acid sequence contained a hydrophobic signal peptide (amino acids 1 to 16 in FIG. 3), but did not contain a membrane anchor domain. The absence of a membrane anchor domain was not unexpected as the antigen was reported to be an exported protein that accumulated in the parasitophorous vacuole. P. Deplace et al., Mol. Biochem. Parasitol., 23:193–201 (1987); P. Delplace et al., Mol. Biochem. Parasitol., 17:239–251 (1985). The protein which is highly acidic has an expected net charge of −35. Serine residues account for 11% of the amino acids in the protein and 57% of those serine residues (62 of 108) were localized within a 201 amino acid sequence (residues 26 to 227) that included a 35-mer polyserine repeat. Forty percent of the amino acid residues in that serine rich segment were either serine or threonine (serine=30%; threonine= 10%). The coding portion of the SERA gene conformed to the known properties of P. falciparum coding regions in that the coding region had a relatively low A+T content (71%), a high A to T ration (1.4), an S-value comparable to that of other *P. falciparum* coding sequences, and an increasing A+T content for the three coding positions (62%, 66%, 86%).

Expression of the SERA Gene in the Parasite

Figure 4:
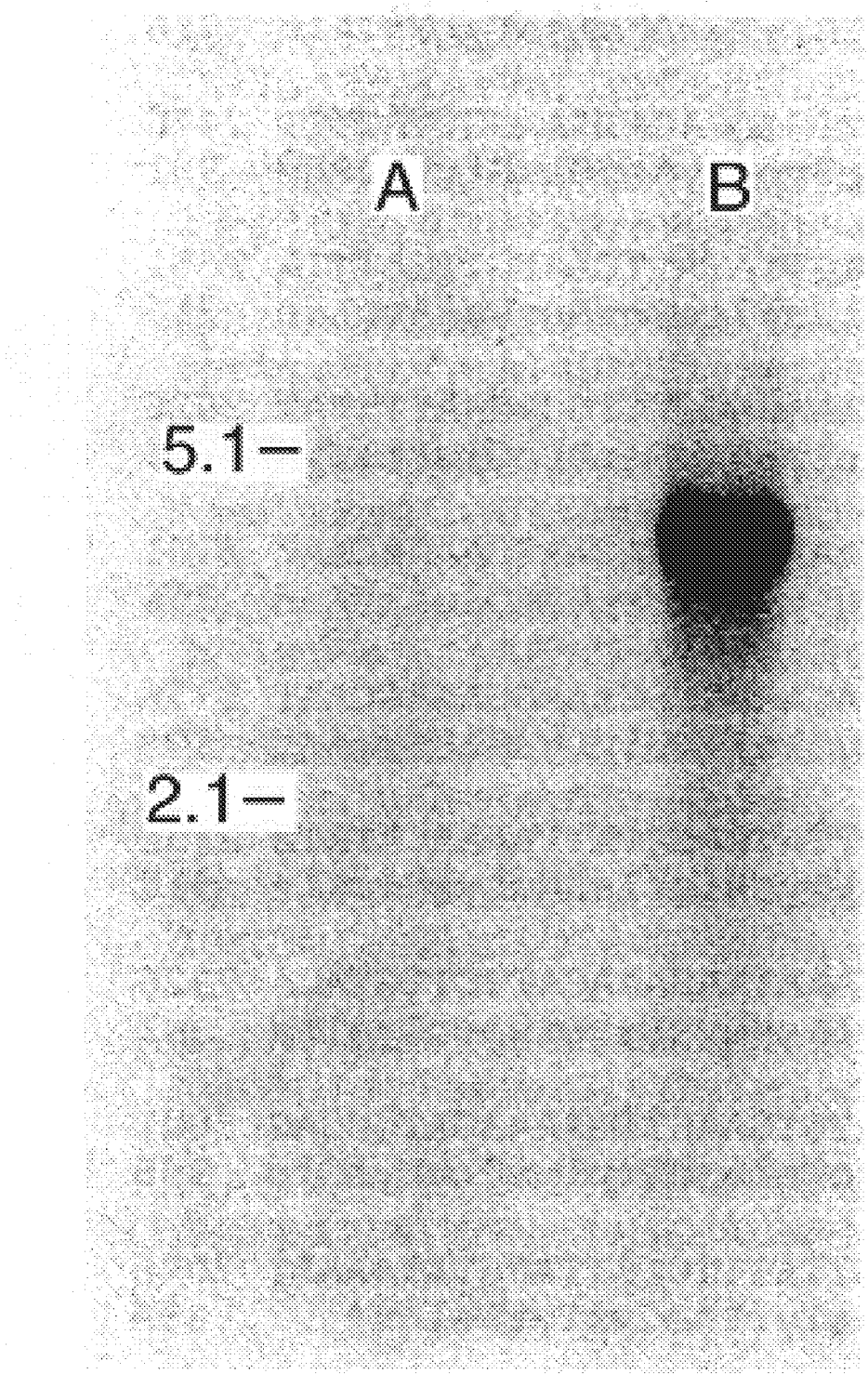
FIG. 4 shows the results of a Northern blot analysis of the SERA gene mRNA. The locations of RNA size markers of 5.1 and 2.1 Kb are shown.

It was previously found that the mRNA for the SERA gene was probably abundant during late trophozoite-schizont stages because a large fraction (1.5%) of cDNA clones in that cDNA library hybridized with cDNA#366. Total RNA was isolated from late trophozoite-schizont stage parasites and was purified into poly (A)⁻ and poly(A)⁺ fractions by oligo-dT affinity chromatography. Northern blot analysis of the SERA mRNA revealed it was a single 4.1 kb species (FIG. 4). It was concluded that the mRNA was apparently very abundant because the 4.1 kb SERA mRNA in the Northern blot was easily detectable autoradiographically, requiring only a one minute exposure of the X-ray film. In addition, on the ethidium bromide stained gel prior to the blotting of the RNA, we could visually detect four stained bands in the smear of parasite mRNA, one of which corresponded in size with the 4.1 kb SERA mRNA. All available evidence suggests that both the SERA mRNA and protein are abundant during late trophozoite-schizont parasite stages.

Nucleotide Sequencing of SERA Genomic DNA

A *P. falciparum* genomic EcoRI library constructed in lambda gt11 was screened with ³²P-labeled cDNA#366 and twelve positive phage clones were isolated. A genomic DNA clone that was plaque purified, clone E31, contained a 4.8 kb DNA insert (FIG. 5). Its sequence was determined and compared to the previously determined nucleotide sequence of the SERA cDNA (FIG. 1). Clone E31 contained sequences 5' to the unique EcoRI site in the SERA gene. Portions of its nucleotide sequence differed significantly from the sequence of the SERA cDNA. Because a 39 bp sequence was present in the SERA cDNA sequence, but was absent in clone E31, it was believed that clone E31 might not represent an expressed form (allele) of the gene that encoded the SERA antigen. To identify possible genomic DNA clones that corresponded to the allele encoding the cDNA defined SERA antigen, a 30 bp single-stranded oligonucleotide (probe A, see Methods section) was synthesized. That 30 base oligonucleotide was the antisense sequence of nucleotides 630 to 659 in the SERA cDNA sequence FIG. 2, and contained part of the 39 bp sequence that was missing from clone E31. Probe A did not hybridize with clone E31.

³²P-labeled probe A was used to re-screen the genomic EcoRI library and eight of 40,000 phage plaques hybridized with probe A. Each of those eight plaque-purified clones contained a 4.8 kb EcoRI fragment that hybridized with the previously characterized SERA cDNA clones, cDNA#366 and cDNA#3102 (FIG. 1 and FIG. 5). One genomic DNA clone, clone E3C (FIG. 5), was subcloned into plasmid pUC19, and it was completely sequenced (nucleotides 1 to 4779 in FIG. 6). The sequence of clone E3C and the previously determined SERA cDNA sequence was identical in the coding region of the SERA gene. This result indicated that probe A specifically hybridized to an allele of the SERA gene that encoded the previously isolated SERA cDNA clones. The comparison of the sequence of clone E3C and clone E31 is summarized in Table II.

TABLE II

Nucleotide Differences Between the Nucleotide Sequence Defined by the cDNA Clones and Clone E3C (allele I), and the Clone E31 (allele II)

| Location[a] | Allele I[b] | Allele II |
|---|---|---|
| 132 | A | C |
| 158 | A | G |
| between 1817 and 1818 | | TATATATATA |
| between 2047 and 2048 | | TT |
| 2151 | A | deleted |
| from 2478 to 2483 | GAAAAA | deleted |
| between 2649 and 2650[c] | | 24 bp insert[d] |
| 3087 | G | A |
| 3092 | A | T |
| 3096 | A | T |
| from 3098 to 3136 | 39 bp[e] | deleted |
| 3140 | C | T |
| 3149 | A | T |
| 3157 | G | A |
| 3185 | T | A |
| 3191 | A | T |
| from 3812 to 3815 | ATAT | deleted |
| 3993 | C | A |

[a]The nucleotide locations are based on the SERA genomic DNA sequence defined by cDNA and clone E3C (allele I) as shown in FIG. 6.
[b]The nucleotide sequence of clone E3C in the SERA coding region and the corresponding cDNA clones are identical. The previously determined SERA cDNA sequence was encoded between nucleotides 2304 and 5867 of the genomic DNA sequence in FIG. 6.
[c]As there are two identical 24-bp sequences in clone E31. This 24 bp insert may either be located between nucleotides 2649 and 2650 or 2673 and 2674.
[d]The 24 bp insert was 5' GTAATACAGGAGGAGGTCAAGCAG 3'.
[e]The 39 bp sequence was 5' GGGAACAGTTAGAGGAGATACAGAAC-CAATTTCAGATTC 3'.

Clone E3C, that encoded the SERA mRNA defined by the previously sequenced SERA cDNA clones, was called allele I, while the clone E31 was considered to represent another SERA gene allele, allele II, not represented in SERA cDNA.

The 3' portion of the SERA gene was previously identified in clone MBN#3102 (FIG. 1 and FIG. 5), which was isolated by using cDNA#3102 to probe a *P. falciparum* MBN genomic DNA library. MBN#3102 was sequenced and its sequence was compared to the 4.8 kb fragments of allele I (clone E3C) and allele II (clone E31), as well as to the corresponding SERA cDNA sequences. The sequence 5' of the EcoRI site in MBN#3102 (FIG. 5) differed from the sequence of clone E3C by 1 nucleotide (nucleotide 3993, Table I) and was identical to the sequence of clone E31. Therefore, MBN#3102 represented allele II DNA (Table II). Because the 1.4 kb sequence 3' of the EcoRI site (FIG. 5) in MBN#3102 was identical to the 3' nucleotide sequence in the SERA cDNA, we concluded that the 3' genomic sequence of allele I was identical to that of allele II. The 6124 bp genomic DNA sequence containing the SERA gene, allele I, is shown in FIG. 6.

Structure of the SERA Gene

The open reading frame which encoded the SERA antigen began with the ATG at nucleotide 2407 and ended at the TAA at nucleotide 5836 (FIG. 6). The SERA gene (allele I and allele II) contained two separate regions of repeated amino acid sequences. One region in allele I which included amino acids 23 to 62 contained 5 copies of a degenerate octamer amino acid repeat. Allele II contained one additional octamer amino acid repeat in that region caused by a 24 bp insert (see Table II). The other amino acid repeat of allele I, which included amino acids 191 to 225, contained a polyserine repeat composed of 35 serine residues. The polyserine repeat was encoded by a hexanucleotide repeat, AG(T or C) TC(A or T). Allele II contained a polyserine repeat of only 34 serine residues because a 39 bp deletion (Table II) removed amino acids 178 to 191 (FIG. 3 and FIG.

6). Amino acid 191 is the first serine residue in the polyserine repeat of allele I. In addition, there were nucleotide differences between allele I and allele II in the polyserine repeat region (Table II, FIG. 6).

There were three large sequences present in SERA genomic DNA that were not found in SERA cDNA (FIG. 6). They were believed to be intron sequences of the SERA gene for several reasons. Those reasons were: a) All the presumed intron sequences contained nucleotides immediately flanking exon borders (FIG. 6) that conformed to the eukaryotic introns GT . . . AG junction rule. Mount, S. M. (1982) *Nucleic Acids Res.*, 10:459–472). All of these presumptive intron sequences had higher A+T contents (85–89%) than the surrounding exons (A+T content 71%); and c) Each presumptive intron sequence contained multiple stop codons in each reading frame. Both SERA gene alleles contained three introns.

The genomic DNA contained a 2406 bp flanking sequence at the 5' end and a 286 bp flanking sequence at the 3' end of the gene. Both 5' and 3' flanking sequences contained higher A+T content (87%) than the coding sequence (71%) and also contained multiple stop codons in all reading frames. These differences between coding and flanking sequences have been observed in other *P. falciparum* genes. Weber, J. L., *Gene*, 52:103–109 (1987). Another open reading frame was found at the 5' end of the clone E3C (FIG. 6) which started within the EcoRI site at the 5' end of the sequence and ended at nucleotide 485. The precise ends of the genomic DNA sequence that encode the SERA gene can not be identified until the 5' and 3' mRNA termini and the SERA gene regulatory elements have been mapped.

Copy Number Analysis of the SERA Gene

Figure 8:
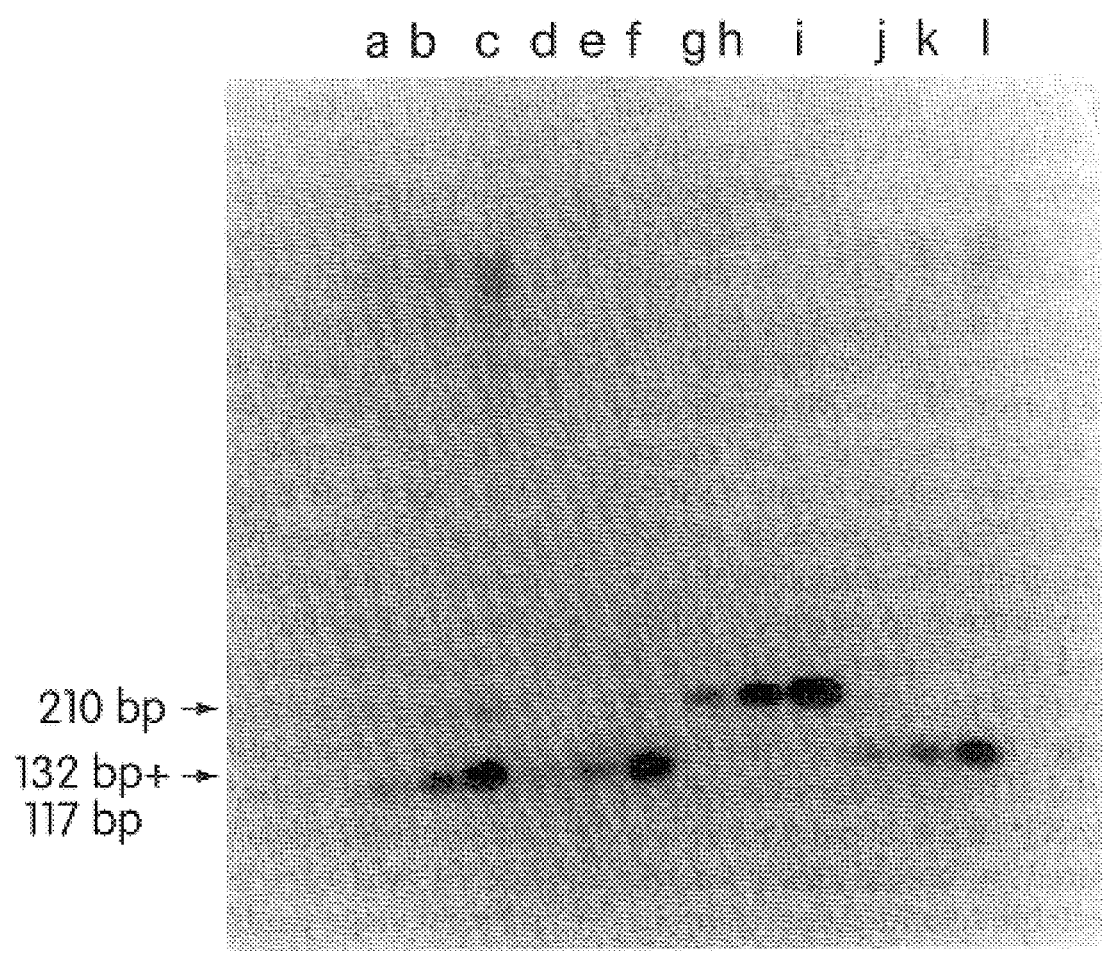
FIG. 8 shows the results of Southern hybridization of HinfI-treated clone E3C, clone E31, FCR3 genomic DNA, and Honduras I genomic DNA with the 210 bp HinfI fragment of allele II (clone E31). Lanes a–c respectively contained 0.9 µg, 1.8 µg and 3.6 µg of FCR3 genomic DNA. Lanes d–f respectively contained 0.225 ng, 0.45 ng and 0.90 ng of clone E3C. Lanes g–i contained clone E31 in the same amounts as lanes d–f. Lanes j–l contained Honduras-1 genomic DNA in the same amounts as lanes a–c. The filter was hybridized with the $^{32}$P-labeled 210 bp HinfI fragment of clone E31. The upper band in lanes a–c and g–i is a 210 bp fragment. The lower broader bands in lanes a–f and j–l contain two fragments (132 bp and 117 bp), which are not well resolved in agarose gels.

One explanation of the previously observed abundance of SERA gene mRNA (allele I) in late trophozoite and schizont stage parasites could be the presence of a high SERA gene copy number. The SERA gene copy number per parasite of allele I and allele II in the chromosomal DNA was therefore determined according to the Wellems method. Wellems, T. E. et al., *Cell*, 49:633–642 (1987). Alleles I and II were discriminated based on the observation that allele I contained an additional and unique HinfI restriction site FIG. 6 and 7, nucleotides 3132–3136) within the 39 bp sequence which was not present in allele II (Table II). Digestion of allele II with HinfI produced only one fragment (210 bp) while digestion of allele I with HinfI produced 2 fragments (117 bp and 132 bp) from that region. The DNA concentration of clone E3C, clone E31, FCR3, and Honduras-1 were quantitated both spectrophotometrically and by agarose gel electrophoresis. A defined amount of clone E3C, clone E31, FCR3, and Honduras-1 DNA was digested with HinfI, electrophoresed, and Southern blotted. The filter was hybridized with the purified and $^{32}$P-labeled 210 bp HinfI fragment of allele II (FIG. 8). Clone E3a (lanes g,h,i) contained only the 210 bp HinfI fragment used as the probe for Southern blot, while clone E3C (lanes d,e,f) contained the 117 bp and 132 bp fragments, which were not well resolved in the agarose gel. HinfI digestion of Honduras-1 genomic DNA produced the 117 bp and the 132 bp fragments only (lanes j,k,l), while digestions of FCR3 genomic DNA produced the 210 bp, 132 bp and 117 bp DNA fragments (lanes a,b,c). The results indicated that FCR3 genomic DNA contained oth alleles, but at unequal levels. A comparison between the binding of the probe to the genomic DNA and to both cloned alleles was made by optical density analysis of the autoradiograms (FIG. 8). The copy number of allele I and allele II was calculated to be 1.3 and 0.2 copies per FCR3 parasite based on the *P. falciparum* genomic size of 30,000 kb. Only allele I of the SERA gene was found in the *P. falciparum* Honduras-1 strain and was detected at a level of 1.1 copy per parasite.

Figure 9:
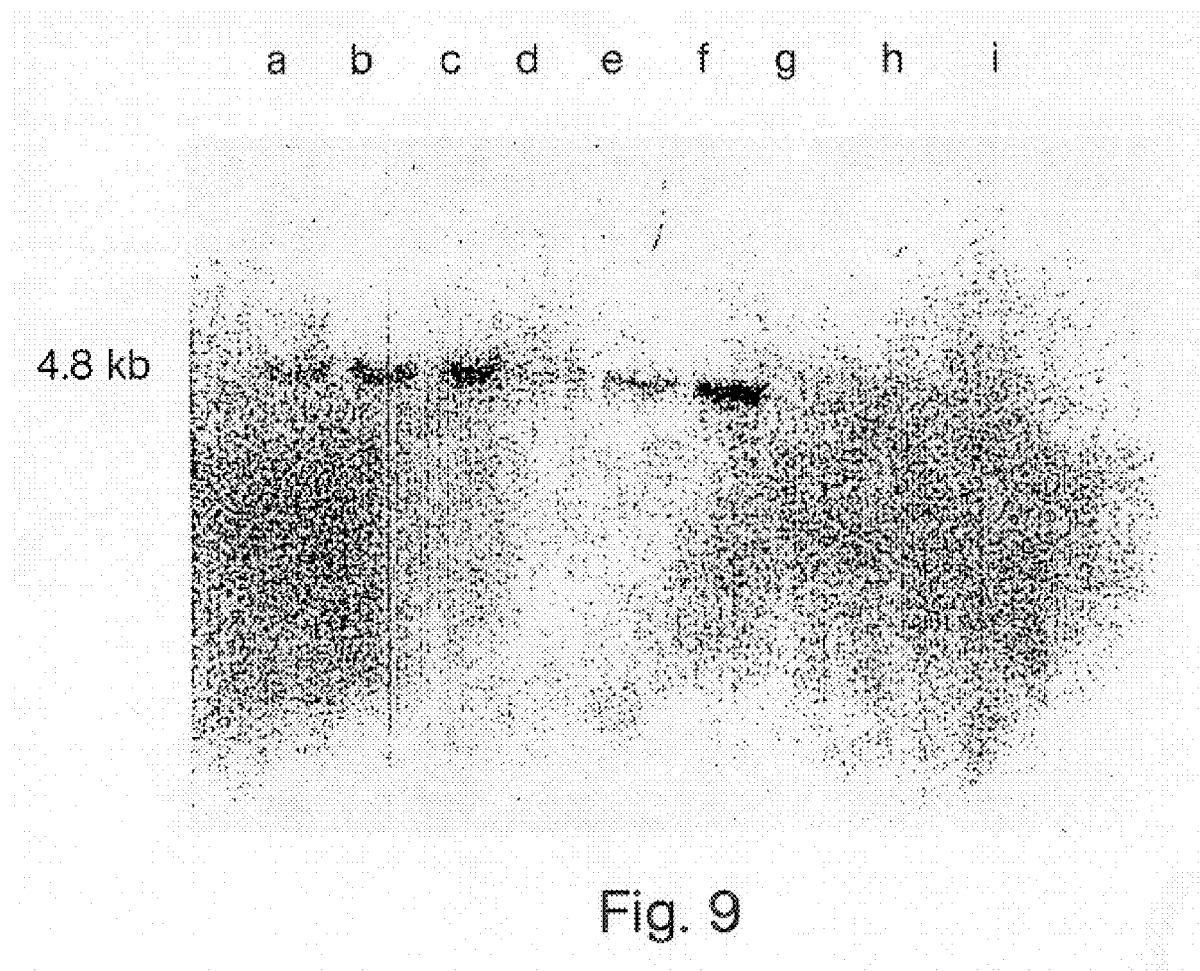
FIG. 9 shows the results of Southern hybridization of EcoRI digested clone E3C, clone E31 and FCR3 genomic DNA. The filter was probed with $^{32}$P-labeled probe A. Lanes a–c respectively contained 1.8 ug, 3.6 ug and 7.2 ug of FCR3 genomic DNA. Lanes d–f respectively contained 0.45 ng, 0.90 ng and 1.8 ng of pUC19 plasmid containing clone E3C. Lanes g–i respectively contained 0.45 ng, 0.90 ng and 1.8 ng of pUC19 plasmid containing clone E31.

The copy number of allele I in FCR3 using probe A (probe A is specific for allele I) was also determined. As expected, probe A only hybridized to allele I (FIG. 9) and the copy number of allele I was determined to be 1.3 copies per parasite.

DISCUSSION

A lambda gt11 cDNA expression library was constructed from poly(A) RNA prepared from trophozoite and schizont enriched cultures of *P. falciparum*. About 1% of the clones containing cDNA inserts expressed antigens that were recognized by a pooled antimalarial Nigerian serum. A cDNA gene bank was established consisting of 288 independent antigen-expressing phage that reacted with parasite inhibitory Nigerian serum that strongly reacts with *P. falciparum* antigens. It was observed that a number of cDNA clones were recognized by a parasite inhibitory mMAb, 43E5. H. Banyal et al., *Am. J. Trop. Med. Hyg.*, 34:1055–1064 (1985).

The cDNA#366 was sequenced and it exhibited a well conserved homology to the partial genomic DNA sequence reported for a *P. falciparum* gene previously designated pl26. J. L. Weber et al., *Molecular Strategies of Parasitic Invasion*, Agabian, Goodman and Nogueira (eds.) p. 379–388, Alan R. Liss, Inc. NY (1987)). We reported the first cDNA sequence for that gene (pl26) and have significantly extended the gene's primary structural information. Their sequence was from a clone isolated from a genomic DNA library of the *P. falciparum* Camp strain screened by a monospecific rabbit antiserum against an "exported" parasite antigen reported to be a 126 kDa protein that was processed into antigens of 50, 47 and 18 kDa that were released into the culture supernatant. DelPlace et al., *Mol. Biochem. Parsitol.*, 23:193–201 (1987). The mMAb 43E5 reacted with antigens of 40 and 35 kd at all stages of development by Western blot analysis, though it reacted with greater intensity of binding to the schizont and merozoite preparations. H. Banyal et al., *Am. J. Trop. Med. Hyg.*, 34:1055–1064 (1985). Some parts of the 126 kDa schizont precursor protein (i.e., 40 and 35 kDa peptides) may remain associated with the schizonts and merozoites and may be the only form of the original protein recognized by mMAb 43E5. With the knowledge of the cDNA and amino acid sequence, we have been able to establish a structural basis for developing a malarial vaccine based upon the SERA gene.

Among the 288 pre-screened Nigerian positive clones, 2.8% (8 clones) reacted with mMAb 43E5 and 5H10. These frequencies might reflect the populations of each antibody in the pooled Nigerian serum that was used for the pre-screening of the original cDNA expression library. The estimation of the frequencies of clones that hybridized with cDNA#366 in the total cDNA library was 1.5%. While neither the frequence of phage plaques that are reactive with the mMAb nor the frequency of plaques that hybridize with the cDNA probe can provide an unambiguous measure of the relative expression of the gene coded for by the cDNAs, the results did suggest that the gene was expressed at relatively high frequencies. This was substantiated by the subsequent Northern blot analysis of the MRNA obtained from trophozoites and schizonts (FIG. 4).

We have subsequently cloned and sequenced the genomic DNA constituting the parasite SERA gene and its flanking sequence. The gene copy number was found to be one per parasite, which means that the high levels of mRNA and SERA protein are most likely related to a strong promoter which should be located in the 5' flanking region of the gene. This sequence should enhance our ability to increase production of the SERA antigen when cloned and expressed in an appropriate host. In addition, the relation of the first SERA gene intron to the signal sequence (FIGS. 5 and 6) provides the potential for manipulating the signal sequence to improve the recovery of the SERA protein from the cloned gene that will be used to produce a genetically engineered protein.

In summary, the defining of the cDNA and gDNA sequences of the *P. falciparum* SERA gene opens a number of avenues for utilization of this knowledge for providing a vaccine and as a source of antigenic material to be used in diagnostic tests.

Equivalents

Those skilled in the art will recognize or be able to ascertain, using no more than routine experimentation, many equivalents to the specific materials and components described herein. Such equivalents are intended to be encompassed in the scope of the following claims.

We claim:

1. A vaccine for reducing the severity of *P. falciparum* malaria in a subject comprising an isolated recombinant SERA (allele I) or SERA (allele II) polypeptide in combination with a pharmaceutically acceptable carrier and optionally an adjuvant, wherein said vaccine elicits parasite inhibitory antibodies that reduce the severity of malaria.

2. The vaccine of claim 1 wherein the SERA polypeptide comprises the sequence of allele I.

3. The vaccine of claim 1 wherein the SERA polypeptide comprises the sequence of allele II.

4. A method for reducing the severity of *P. falciparum* malaria in a subject comprising administering to the subject an immunogenic amount of the vaccine of claim 1.

5. A method of producing a parasite-inhibitory antibody in a parasite host comprising immunizing said host with the vaccine of claim 1 wherein said antibody reduces the severity of *P. falciparum* malaria.

* * * * *